(12) United States Patent
Kataoka et al.

(10) Patent No.: US 10,379,334 B2
(45) Date of Patent: *Aug. 13, 2019

(54) LIGHT MEASUREMENT DEVICE, LIGHT MEASUREMENT METHOD, AND LIGHT MEASUREMENT PROGRAM

(75) Inventors: Takuji Kataoka, Hamamatsu (JP); Masanori Matsubara, Hamamatsu (JP)

(73) Assignee: HAMAMATSU PHOTONICS K.K., Hamamatsu-shi, Shizuoka (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/127,669

(22) PCT Filed: Jun. 19, 2012

(86) PCT No.: PCT/JP2012/065637
§ 371 (c)(1),
(2), (4) Date: Feb. 11, 2014

(87) PCT Pub. No.: WO2012/176775
PCT Pub. Date: Dec. 27, 2012

(65) Prior Publication Data
US 2014/0152798 A1     Jun. 5, 2014

(30) Foreign Application Priority Data

Jun. 21, 2011 (JP) .................. 2011-137314

(51) Int. Cl.
*H04N 7/18* (2006.01)
*G02B 21/36* (2006.01)
(Continued)

(52) U.S. Cl.
CPC ....... *G02B 21/365* (2013.01); *G01N 21/6452* (2013.01); *G01N 21/6458* (2013.01);
(Continued)

(58) Field of Classification Search
CPC .......... G01N 21/6452; G01N 21/6458; G02B 21/365; G06T 7/0016; G06T 2207/30242;
(Continued)

(56) References Cited

U.S. PATENT DOCUMENTS

| 5,047,846 A | 9/1991 | Uchiyama et al. |
| 6,462,771 B1 | 10/2002 | Kitagawa |

(Continued)

FOREIGN PATENT DOCUMENTS

| CN | 1690696 | 11/2005 |
| CN | 101712926 | 5/2010 |

(Continued)

OTHER PUBLICATIONS

James Ross, "Microstimulation and Multicellular Analysis: A Neutral Interfacing System for Spatiotemporal Stimulation", In: "PHD Thesis", Institute of Technology, Department of Biological Engineering, Georgia Institute of Technology, Aug. 1, 2008, p. 1-p. 151, XP055171705.

(Continued)

*Primary Examiner* — Jayanti K Patel
*Assistant Examiner* — Richard B Carter
(74) *Attorney, Agent, or Firm* — Drinker Biddle & Reath LLP

(57) ABSTRACT

A light measurement device is a light measurement device for measuring light coming from a sample, and is provided with a moving-image acquisition part for acquiring moving image data, and an analysis processing part for performing analysis processing on moving image data. The analysis processing part includes: a luminance-value-data acquisition part for acquiring luminance value data indicating a chronological change in a luminance value; a luminance-value extraction part for extracting a peak value and a bottom value of the luminance value, from the luminance value (Continued)

data; and a pixel specifying part for calculating an evaluation value evaluating a state of a change in a luminance value on the basis of the peak value and the bottom value and specifying a target pixel that is to be analyzed from a plurality of pixels on the basis of a repeat state of the evaluation value.

4 Claims, 14 Drawing Sheets

(51) Int. Cl.
    *G01N 21/64*     (2006.01)
    *G06T 7/00*     (2017.01)

(52) U.S. Cl.
    CPC .. *G06T 7/0016* (2013.01); *G06T 2207/10016* (2013.01); *G06T 2207/10056* (2013.01); *G06T 2207/30024* (2013.01); *G06T 2207/30242* (2013.01)

(58) Field of Classification Search
    CPC . G06T 2207/10016; G06T 2207/10056; G06T 2207/30024
    USPC ........... 348/79; 359/368; 382/382, 133, 282, 382/103; 424/93.7; 435/7.1
    See application file for complete search history.

(56) References Cited

U.S. PATENT DOCUMENTS

| | | | |
|---|---|---|---|
| 2004/0241832 A1 | 12/2004 | Muraki et al. | |
| 2006/0018013 A1* | 1/2006 | Suzuki | G01N 21/6452 359/368 |
| 2007/0059763 A1* | 3/2007 | Okano | G01N 33/566 435/7.1 |
| 2008/0056610 A1* | 3/2008 | Kanda | G02B 21/365 382/282 |
| 2009/0141960 A1* | 6/2009 | Yamamoto | G01N 21/6458 382/133 |
| 2010/0253774 A1* | 10/2010 | Yoshioka | G02B 21/16 348/79 |
| 2010/0295932 A1* | 11/2010 | Yokomachi | G06T 5/008 348/79 |
| 2010/0322906 A1* | 12/2010 | Matsuyama | C12N 5/0676 424/93.7 |
| 2011/0135171 A1 | 6/2011 | Galigekere et al. | |
| 2011/0266074 A1* | 11/2011 | Fan | G06F 3/0418 178/18.09 |
| 2011/0310239 A1* | 12/2011 | Ogihara | H04N 5/243 348/79 |
| 2013/0322688 A1* | 12/2013 | Tsuchiya | G08G 1/167 382/103 |
| 2014/0152798 A1 | 6/2014 | Kataoka et al. | |
| 2014/0152799 A1* | 6/2014 | Kataoka | G06T 7/0016 348/79 |

FOREIGN PATENT DOCUMENTS

| | | |
|---|---|---|
| CN | 101782524 | 7/2010 |
| JP | S63-233392 A | 9/1988 |
| JP | 2000-275529 | 10/2000 |
| JP | 2000-275539 A | 10/2000 |
| JP | 2003-014737 A | 1/2003 |
| JP | 2005-027623 A | 2/2005 |
| JP | 2005-102629 | 4/2005 |
| JP | 2005-291720 | 10/2005 |
| JP | 2006-200987 A | 8/2006 |
| JP | 2006-340686 | 12/2006 |
| JP | 2007-121106 A | 5/2007 |
| JP | 2007-278984 | 10/2007 |
| JP | 2007-278985 A | 10/2007 |
| JP | 5869239 B2 | 2/2016 |
| WO | WO 2007/013551 | 2/2007 |
| WO | WO 2010/143420 | 12/2010 |

OTHER PUBLICATIONS

Knut Holthoff et al., "Rapid time course of action potentials in spines and remote dendrites of mouse visual cortex neurons", The Journal of Physiology, vol. 588, No. 7, Mar. 30, 2010, p. 1085-p. 1096, XP055172422.

U.S. Office Action dated Mar. 31, 2016 that issued in U.S. Appl. No. 14/127,700 including Double Patenting Rejections on pp. 4-7.

U.S. Office Action dated Jun. 6, 2017 that issued in U.S. Appl. No. 14/127,700 including Double Patenting Rejections on pp. 2-5.

* cited by examiner (a)

(b)

(c)

(d)

(e)

(a)

(b)

(a)

(b)

(a)

(b)

(a)

(b)

LIGHT MEASUREMENT DEVICE, LIGHT MEASUREMENT METHOD, AND LIGHT MEASUREMENT PROGRAM

TECHNICAL FIELD

The present invention relates to a light measurement device for measuring light emitted from a myocardial cell, a light measurement method, and a light measurement program.

BACKGROUND ART

In the drug development field, there is a case where an influence of a medicine administered to a sample such as a myocardial cell is evaluated on the basis of light emitted from the sample. Patent Literature 1 discloses a light measurement device capable of improving measurement sensitivity to light coming from a sample. In this device, in a measurement region set corresponding to a well on a light detection image, a two-dimensional luminance value distribution within the measurement region and a predetermined luminance value threshold value are compared so as to extract from a measurement region an analysis region on which analysis processing is to be performed. Analysis processing is performed by using data of the luminance value within the analysis region as analysis data.

CITATION LIST

Patent Literature

Patent Literature 1: Japanese Patent Application Laid-Open No. 2007-278985

SUMMARY OF INVENTION

Technical Problem

In the light measurement device described in Patent Literature 1, when a pixel to be analyzed is specified, a two-dimensional luminance value distribution within a measurement region and a predetermined luminance value threshold value are compared so as to extract the analysis region. Thus, when a myocardial cell and a cell that is not a myocardial cell are in the measurement region and both emit light having a luminance value exceeding a luminance value threshold value, it is difficult to set only the region of the myocardial cell as the analysis region. Further, the myocardial cell beats and the region of the myocardial cell temporally alters, and, it is thus difficult to set a boundary of the myocardial cell.

In view of the above-described problem, it is an object of the present invention to provide a light measurement device with which it is possible to specify a pixel configuring an image of a myocardial cell in which a luminance value temporally alters in an, image including light emitted from a sample including the myocardial cell, a light measurement method, and a light measurement program.

Solution to Problem

A light measurement device according to one aspect of the present invention is a light measurement device for measuring light emitted from a myocardial cell held by a sample case having a holding part for holding a sample including a myocardial cell. The device is provided with: a moving-image acquisition means for acquiring moving image data of a two-dimensional light image by detecting a two-dimensional light image of a sample case including light emitted from a sample held inside a holding part of the sample case; and an analysis processing means for performing analysis processing on the moving image data. The analysis processing means includes: a luminance-value-data acquisition means for acquiring luminance value data indicating a temporal alteration in a luminance value in the plurality of pixels configuring a region corresponding to the holding part, from a region corresponding to the holding part included in the moving image data; a luminance-value extraction means for extracting a peak value and a bottom value of the luminance value from the luminance value data; and a pixel specifying means for calculating an evaluation value evaluating the temporal alteration, of the luminance value, repeatedly appearing in the luminance value data on the basis of the peak value and the bottom value and specifying a target pixel configuring an image of the myocardial cell from the plurality of pixels on the basis of the evaluation value.

A light measurement method according to one aspect of the present invention is a light measurement method for measuring light emitted from a myocardial cell held by a sample case having a holding part for holding a sample including the myocardial cell. The method comprises: a moving-image acquisition step of acquiring moving image data of a two-dimensional light image by detecting a two-dimensional light image of a sample case including light emitted from the sample held inside a holding part of a sample case; and an analysis processing step of performing analysis processing on the moving image data. The analysis processing step includes: a luminance-value-data acquisition step of acquiring luminance value data indicating a temporal alteration in a luminance value in a plurality of pixels configuring a region corresponding to the holding part, from a region corresponding to a holding part included in the moving image data; a luminance-value extraction step of extracting a peak value and a bottom value of a luminance value from the luminance value data; and a pixel specifying step of calculating an evaluation value evaluating the temporal alteration, of the luminance value, that repeatedly appears in the luminance value data on the basis of the peak value and the bottom value and specifying a target pixel configuring an image of a myocardial cell from a plurality of pixels on the basis of the evaluation value.

A light measurement program according to one aspect of the present invention is a light measurement program for measuring light emitted from a myocardial cell held by a sample case having a holding part for holding a sample including the myocardial cell. The program causes a computer to function as: a luminance-value-data acquisition means for acquiring luminance value data indicating temporal alteration in a luminance value in a plurality of pixels configuring a region corresponding to a holding part, from a region corresponding to a holding part included in moving image data, relative to moving image data which is acquired by a moving image acquisition means and in which a two-dimensional light image of a sample case including light emitted from a sample held inside a holding part of the sample case is detected; a luminance-value extraction means for extracting a peak value and a bottom value of a luminance value from the luminance value data; and a pixel specifying means for calculating an evaluation value evaluating the temporal alteration, of the luminance value, repeatedly appearing in the luminance value data on the basis of the peak value and the bottom value and specifying a target pixel configuring an image of the myocardial cell from the plurality of pixels on the basis of the evaluation value.

According to the light measurement device, the light measurement method, or the light measurement program, a two-dimensional light image of a sample case including light coming from a sample including a myocardial cell held inside a holding part of the sample case is detected and the two-dimensional moving image data is acquired. Next, the luminance value data indicating a temporal alteration in the luminance value in a plurality of pixels configuring the moving image data is acquired, and from the luminance value data, the peak value and the bottom value of the luminance value are acquired. Then, on the basis of the peak value and the bottom value, the pixel configuring the image of the myocardial cell to be analyzed is specified. Therefore, it is possible to specify the pixel configuring the image of the myocardial cell from which light having a temporally altering luminance value is repeatedly emitted.

In the light measurement device according to one aspect of the present invention, the evaluation value may be an amplitude of the luminance value obtained from a difference between the peak value and the bottom value. According thereto, the amplitude of the luminance value is zero in a pixel in a region from which light having a fixed luminance value is emitted, and, when a predetermined amplitude threshold value is set, it thus becomes possible to specify only a pixel having an amplitude of the luminance value equal to or more than a threshold value. Therefore, it is possible to preferably specify the pixel configuring the image of the myocardial cell from which light having a temporally altering luminance value is repeatedly emitted.

In the light measurement device according to one aspect of the present invention, the evaluation value may be a change ratio of the luminance value obtained from a ratio of a peak value relative to a bottom value. According thereto, the change ratio of the luminance value in the pixel in a region from which light having a fixed luminance value is emitted is 1, and, when a predetermined change-rate threshold value is set, it thus becomes possible to specify only a pixel having a change ratio of the luminance value equal to or more than a threshold value. Therefore, it is possible to preferably specify the pixel configuring the image of the myocardial cell from which light having a temporally altering luminance value is repeatedly emitted.

In the light measurement device according to one aspect of the present invention, the pixel specifying means may specify the target pixel on the basis of the number of times that the evaluation value exceeds a threshold value acquired in advance. According thereto, it is possible to more preferably specify a pixel configuring an image of a myocardial cell from which light having a temporally altering luminance value is repeatedly emitted.

In the light measurement device according to one aspect of the present invention, the pixel specifying means may specify the target pixel by comparing an average value of the evaluation value and the threshold value acquired in advance. According thereto, it is possible to more preferably specify a pixel from which light having a temporally altering luminance value is repeatedly emitted.

In the light measurement device according to one aspect of the present invention, the analysis processing means may further include a data processing means for using, as the analysis data, the luminance value data of a target pixel and performing analysis processing on luminance value data. According thereto, it is possible to perform an evaluation by using the luminance value data of the pixel configuring an image of a myocardial cell specified by a pixel specifying part. Therefore, it is possible to perform analysis processing in which measurement sensitivity to the light emitted from the myocardial cell is improved.

Advantageous Effects of Invention

According to a light measurement device, a light measurement method, and a light measurement program based on the present invention, it is possible to specify a pixel configuring an image of a myocardial cell having a temporally altering luminance value in an image including light emitted from a sample.

DESCRIPTION OF EMBODIMENTS

Hereinafter, with reference to the attached drawings, an embodiment of a light measurement device, a light measurement method, and a light measurement program will be described in detail. It should be noted that in the description of drawings, the same reference sign is given to the same element, and duplicate explanations are omitted.

Figure 1:
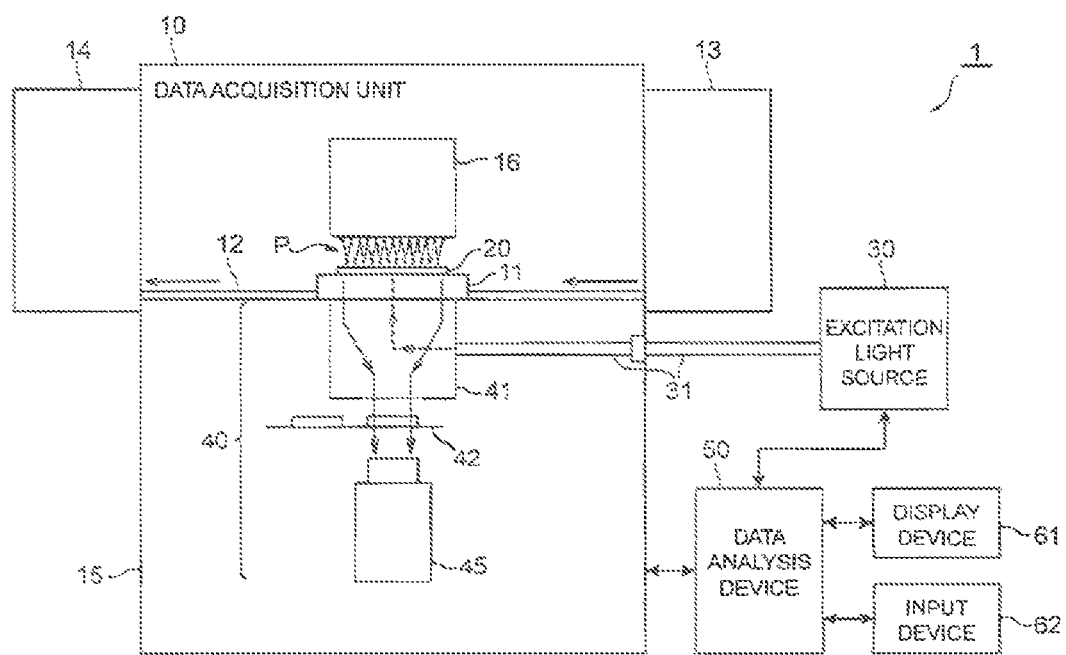
FIG. 1 is a diagram schematically showing one embodiment of a light measurement device.
Figure 2:
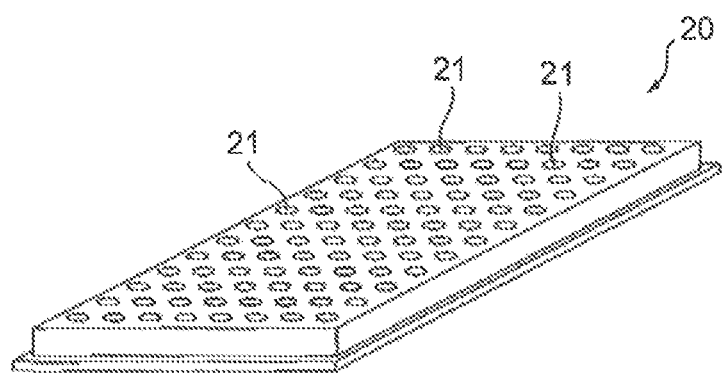
FIG. 2 is a diagram showing one example of the configuration of a micro plate.
Figure 3:
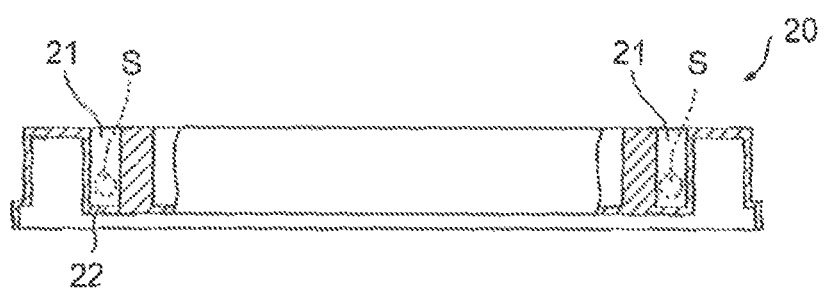
FIG. 3 is a diagram showing a sectional structure obtained when the micro plate in FIG. 2 is viewed laterally.

FIG. 1 is a diagram schematically showing the configuration of one embodiment of a light measurement device 1. FIG. 2 is a diagram showing one example of the configuration of a micro plate 20. FIG. 3 is a diagram showing a sectional structure obtained when the micro plate 20 shown in FIG. 2 is viewed laterally. The light measurement device 1 according to one embodiment may use the micro plate 20 that is one example of a sample case. The light measurement device 1 is a device for measuring a fluorescence from a sample S (see FIG. 3) that is held by the micro plate 20 and arranged at a measurement position P.

The sample S is a cell including a myocardial cell. The light measurement device, the light measurement method, and the light measurement program according to one embodiment can be generally applied not only to the fluorescence measurement but also to a light measurement where light coming from a sample is measured such as a phosphorescence and a light emission. The configuration of the light measurement device 1 will be described below.

As shown in FIG. 1, the light measurement device 1 is configured by including a data acquisition unit 10, an excitation light source 30 and a data analysis device 50. The data acquisition unit 10 includes a black box 15 and a moving-image acquisition part 40. The black box 15 houses therein the micro plate 20 for holding therein the sample S including a myocardial cell subject to fluorescence measurement. The moving-image acquisition part 40 measures the fluorescence from the sample S arranged inside the black box 15 and arranged at the measurement position P.

As shown in FIG. 2 and FIG. 3, the micro plate 20 that is used as a sample case of one embodiment is a planar member in which a plurality of wells (holding part) 21 are arranged in parallel in a two-dimensional array manner. Each of the plurality of wells 21 is configured so that the sample S can be held. For example, as shown in FIG. 2, as the plurality of wells 21, 8×12=96 wells 21 are arranged in a two-dimensional array manner. The shape of the well 21 may be circular or rectangular. A bottom surface 22 of the micro plate 20 is formed of a material through which excitation light for fluorescence measurement entering, with irradiation, into the sample S and a fluorescence emitted from the sample S can pass. It should be noted that generally, the bottom surface 22 of the micro plate 20 provided in the light measurement device 1 may be formed of a material through which light from the sample S, which is to be measured, can pass.

Inside the black box 15, the micro plate 20 is installed. The micro plate 20 is held by a micro plate holder 11 having an opening for fluorescence observation. Inside the black box 15, a micro-plate conveyance mechanism 12 is installed. The micro-plate conveyance mechanism 12 conveys the holder 11 holding the micro plate 20 in a predetermined direction within the black box 15. The predetermined direction is a direction from the right side toward the left side in FIG. 1.

An import-side micro plate stocker 13 is arranged at one side of the black box 15 which is an import side relative to the conveyance direction of the micro plate 20. The import-side micro plate stocker 13 stocks a predetermined number (for example, 25) of unmeasured micro plates 20 which holds the sample S. An export-side micro plate stocker 14 is arranged at the other side of the black box 15 which is an export side relative to the conveyance direction of the micro plate 20. The export-side micro plate stocker 14 stocks the measured micro plates 20.

In such a configuration, the micro plate 20 imported from the import-side micro plate stocker 13 into the black box 15 is being held by the micro plate holder 11 and conveyed by the conveyance mechanism 12. Then, the micro plate 20 is once stopped at the measurement position P, and in this state, the required light measurement is performed on the sample S held by the micro plate 20. After the measurement has been completed, the micro plate 20 is again conveyed by the conveyance mechanism 12, and exported to the export-side micro plate stocker 14. In FIG. 1, a specific configuration illustration of the conveyance mechanism 12 for importing, conveying and exporting the micro plate 20 and the stockers 13 and 14 is omitted.

A dispensing device 16 is arranged above the measurement position P. The dispensing device 16 dispenses a reagent, etc., into the well 21 of the micro plate 20. The measurement position P is a position at which the micro plate 20 and the sample S held thereby are arranged when the fluorescence measurement is executed. The moving-image acquisition part 40 detects the fluorescence emitted via the bottom surface 22 of the micro plate 20 from the sample S housed inside the well 21.

The moving-image acquisition part 40 is a moving-image acquisition means for acquiring moving image data of a two-dimensional light image. The moving-image acquisition part 40 detects a two-dimensional light image including a light image from the plurality of wells 21 of the micro plate 20 including the light from the sample S held within the well 21 of the micro plate 20. The two-dimensional light image includes the light emitted from the sample S held inside the well 21 of the micro plate 20. The moving-image acquisition part 40 has an image pickup device 45 capable of acquiring a fluorescence image which is a two-dimensional light detection image by the fluorescence emitted from the sample S. The moving-image acquisition part 40 has a two-dimensional pixel structure in which a plurality of pixels are two-dimensionally arrayed. As the image pickup device 45, for example, a highly sensitive CCD camera or a CMOS image camera may be used. Where necessary, the moving-image acquisition part 40 may include an image amplifying tube, a relay lens, etc., arranged before the image pickup device 45.

A light-guiding optical system 41 is arranged between the measurement position P at which the micro plate 20 is arranged and the image pickup device 45. The light-guiding optical system 41 is an optical system for guiding the two-dimensional light image obtained when the micro plate 20 in which the sample S is held in each of the plurality of wells 21 is viewed from the bottom surface 22 side, toward the image pickup device 45. As for specific configuration of the light-guiding optical system 41, it is possible to appropriately configure the light-guiding optical system 41 by an optical element capable of realizing a required function (for example, a light-collection function and a light-image-reduction function) according to a configuration, etc., of the micro plate 20 and the image pickup device 45. For such an optical element, an optical element having an optical reduction function of imparting a resolution where there are at least one pixel per one cell may suffice. For example, a taper fiber may be adopted (see Japanese Patent Application Laid-Open No. 2001-188044).

An optical filter part 42 is arranged between the light-guiding optical system 41 and the image pickup device 45. The optical filter part 42 arranges, switches, etc., the optical filter onto a light-guiding path of the fluorescence, where necessary, between the light-guiding optical system 41 and the image pickup device 45. However, when such an optical filter part 42 is not necessary, the optical filter part 42 may be omitted.

The light measurement device 1 includes the excitation light source 30. The excitation light source 30 is an excitation-light supply means for supplying the sample S with excitation light for fluorescence measurement. It is possible to appropriately configure the excitation light source 30 according to types of the sample S subject to the fluorescence measurement, a wavelength of the excitation light entering, with irradiation, the sample S, etc. It is possible to configure the excitation light source 30 by an illumination light source for supplying light and an optical filter part for selecting or switching the wavelength of the excitation light, for example. When it is not necessary to supply the excitation light depending on types of light measurement performed on the sample S, the light measurement device 1 may be configured so that the excitation light source 30 is not arranged.

As shown in FIG. 1, the excitation light source 30 is arranged outside the black box 15. The excitation light supplied from the excitation light source 30 enters, with irradiation, the sample S via an excitation-light-supplying light guide 31 and the light-guiding optical system 41. With such a configuration, the light-guiding optical system 41 is an optical system capable of guiding the two-dimensional light image from the micro plate 20 and the sample S to the image pickup device 45, and guiding the excitation light from the excitation light source 30 to the sample S. Such a light-guiding optical system 41 can be configured by using, for example, a dichroic mirror, for passing the fluorescence from the micro plate 20 and reflecting the excitation light from the excitation light source 30. It should be noted that in FIG. 1, optical paths of the fluorescence and the excitation light in the light-guiding optical system 41 are schematically shown by using a solid line and a dotted line, respectively.

The light measurement device 1 includes a data analysis device 50. The data analysis device 50 is an analysis processing means for performing analysis processing on the moving image data including the light detection image acquired by the moving-image acquisition part 40. The data analysis device 50 controls an operation of each part of the data acquisition unit 10 and the excitation light source 30 so as to control a fluorescence measurement on the sample S in the light measurement device 1. As shown in FIG. 1, to the data analysis device 50, a display device 61 for displaying measurement results, etc., and an input device 62 used for data input, input of a necessary instruction for the fluorescence measurement, etc., are connected.

In the above-described configuration, the excitation light for fluorescence measurement enters, with irradiation, the sample S. The excitation light is supplied from the excitation light source 30 via the light guide 31 and the light-guiding optical system 41. The sample S is held within the well 21 of the micro plate 20 and located at the measurement position P within the black box 15. Then, the two-dimensional light image including the fluorescence emitted from the sample S is guided to the image pickup device 45 via the light-guiding optical system 41, and moving image data of the two-dimensional light image is acquired at a predetermined frame rate by the image pickup device 45. The moving image data including the fluorescence image acquired by the moving-image acquisition part 40 is sent to the data analysis device 50. Then, the data analysis device 50 specifies the pixel configuring an image of a myocardial cell, from the input moving image data, and performs thereon analysis processing necessary for evaluation, etc.

The sample case is not limited to the above-described micro plate 20. The plurality of samples S may be held in a dish such as a petri dish as the sample case. Further, the light measurement device 1 may be configured as a device for observing a sample held in the petri dish via a microscope.

Figure 4:
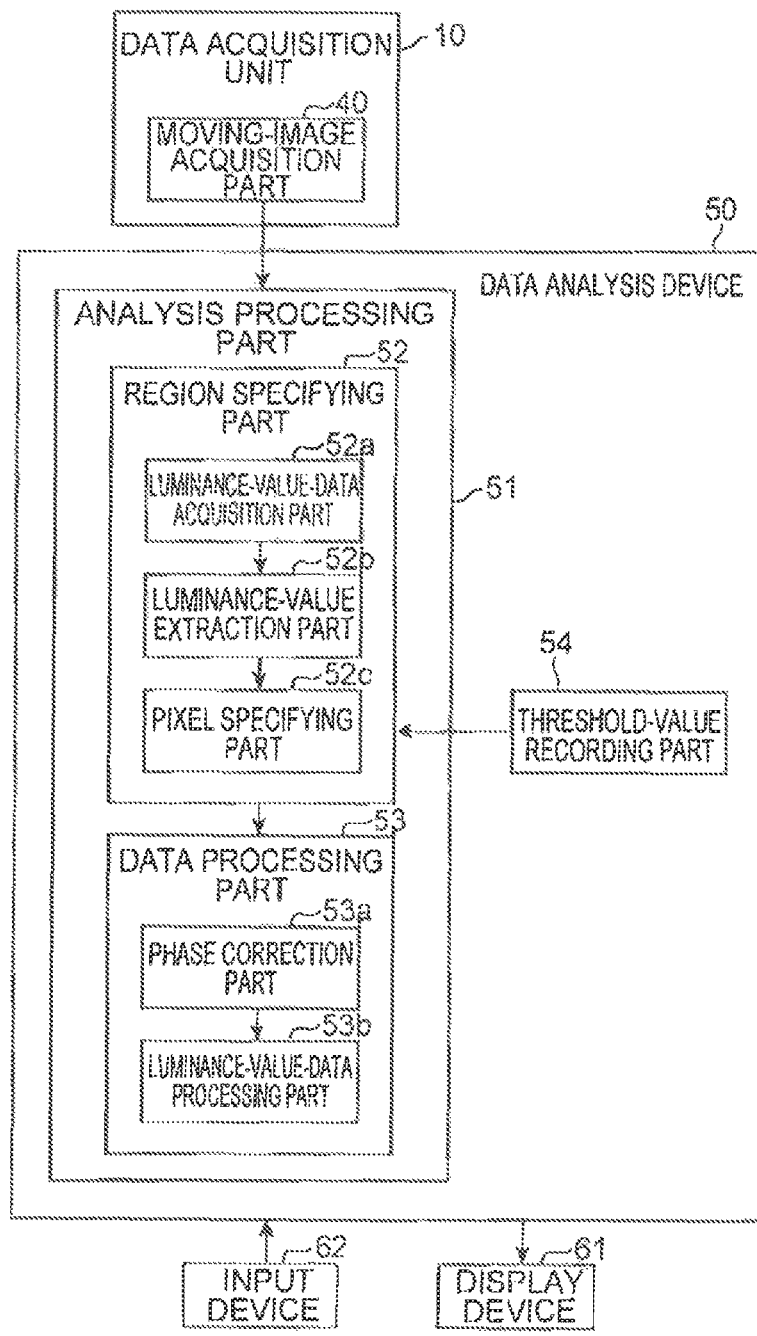
FIG. 4 is a diagram showing one example of the configuration of a data analysis device.

FIG. 4 is a diagram showing a schematic configuration of the data analysis device 50 provided in the light measurement device 1.

The data analysis device 50 is an information processing device for acquiring the luminance value data for each pixel from the moving image data, specifying a target pixel configuring an image of a myocardial cell to be analyzed on the basis of the luminance value data, and implementing predetermined analysis processing on the target pixel. The moving image data is obtained by converting the image obtained by photographing the micro plate 20 including the light emitted from the sample S held within the above-described well 21, into digital data. The moving image data may be input to the data analysis device 50 via a communication network or a recording medium such as a CD-ROM, a DVD and a semiconductor memory.

The data analysis device 50 includes an analysis processing part 51 and a threshold-value recording part 54, as a functional constituent element. The data analysis device 50 is connected to the data acquisition unit 10, the display device 61 and the input device 62.

The analysis processing part 51 includes a region specifying part 52 and a data processing part 53, as a functional constituent element. The analysis processing part 51 specifies the target pixel configuring an image of a cell such as a myocardial cell from the moving image data of the sample S acquired by the moving-image acquisition part 40 of the data acquisition unit 10. The analysis processing part 51 is an analysis processing means for using, as the analysis data, the luminance value data provided in the target pixel and performing analysis processing on the luminance value data. The analysis processing part 51 is connected to the threshold-value recording part 54.

The region specifying part 52 includes a luminance-value-data acquisition part (luminance-value-data acquisition means) 52*a*, a luminance-value extraction part (luminance-value extraction means) 52*b* and a pixel specifying part (pixel specifying means) 52*c*. The region specifying part 52 specifies a target pixel configuring an image of a cell such as a myocardial cell from a measurement region corresponding to the well 21, on the basis of a feature value of a waveform of a temporal alteration in the luminance value provided in the pixel in the moving image data. Examples of the feature value include a peak value and a bottom value of a waveform of a temporal alteration in the luminance value. The region specifying part 52 is connected to the data processing part 53.

The threshold-value recording part 54 records a threshold value used when the target pixel is specified. Examples of the threshold value include a peak-value threshold value, an amplitude threshold value and a change-rate threshold value. The threshold-value recording part 54 is configured so as to be referenced from the region specifying part 52.

The luminance-value-data acquisition part 52*a* acquires the luminance value data in a plurality of pixels configuring a region corresponding to a plurality of wells 21, from a region corresponding to the plurality of wells 21 included in the moving image data input from the moving-image acquisition part 40. The luminance value data indicates a temporal alteration in the luminance value provided in the pixel. The luminance-value-data acquisition part 52*a* regards a region including an image of the well 21 as one measurement region, and acquires the luminance value data for each pixel configuring the measurement region. The luminance value data acquired in the luminance-value-data acquisition part 52*a* is output to the luminance-value extraction part 52*b*.

The luminance-value extraction part 52*b* extracts the peak value and the bottom value on the basis of luminance value data of the pixel input from the luminance-value-data acquisition part 52*a*. The peak value and the bottom value are output to the pixel specifying part 52*c*.

The pixel specifying part 52*c* specifies the target pixel configuring an image of a myocardial cell on the basis of the peak value and the bottom value input from the luminance-value extraction part 52*b*. Information of the target pixel is output to the data processing part 53. A method of specifying the target pixel will be described in detail later.

The data processing part (data processing means) 53 includes a phase correction part 53a and a luminance-value-data processing part 53b. The data processing part 53 refers to the target pixel specified in the region specifying part 52, uses, as the analysis data, the luminance value data provided in the target pixel, and performs the analysis processing on the target pixel configuring an image of a myocardial cell. The data processing part 53 is connected to the region specifying part 52.

The phase correction part 53a corrects a timing at which the bottom value is changed to the peak value in the luminance value data to align the phase of the luminance value data for each pixel. The luminance value data corrected by the phase correction part 53a is output to the luminance-value-data processing part 53b.

The luminance-value-data processing part 53b processes the luminance value data corrected in phase by the phase correction part 53a, for each well 21, for example. The luminance value data processed, for each well 21, by luminance-value-data processing part 53b is output to the display device 61.

Figure 5:
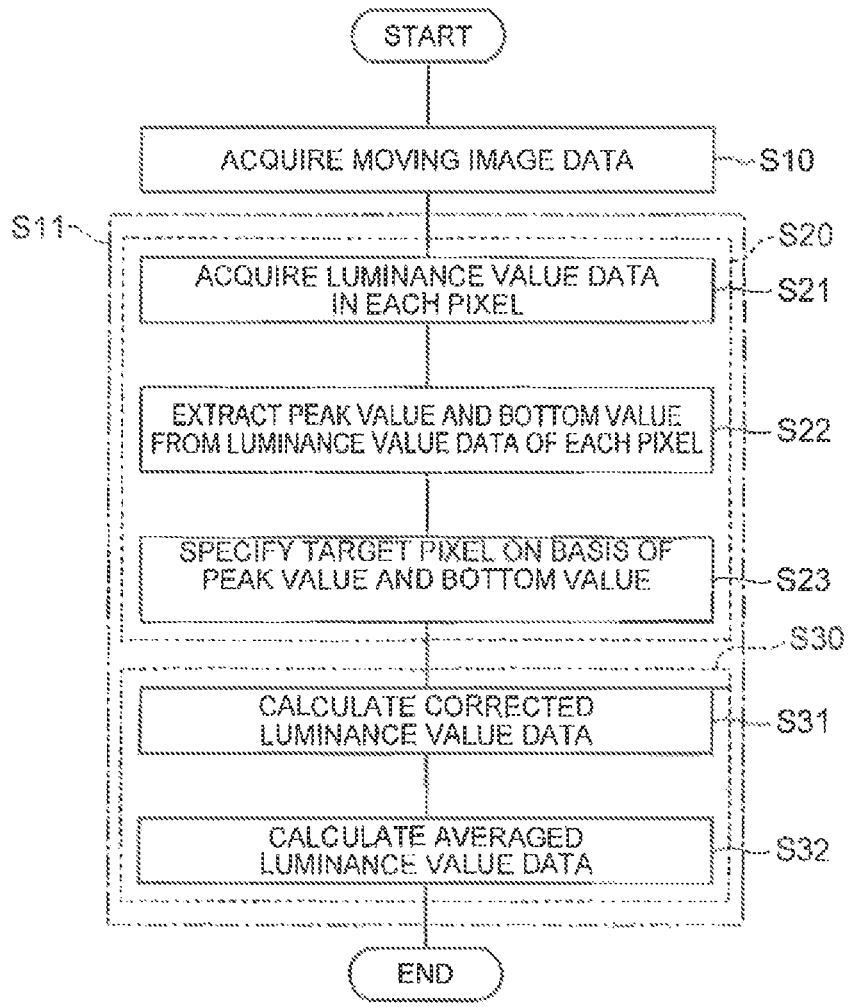
FIG. 5 is a diagram showing one embodiment of a light measurement method.

Next, the light measurement method executed by the light measurement device 1 according to one embodiment will be described, and the light measurement method according to one embodiment will be described in detail. In this case, a step of specifying the target pixel configuring an image of a myocardial cell from the moving image data will be described. FIG. 5 is a diagram for describing major steps of the light measurement method according to one embodiment.

Step S10 is executed by the moving-image acquisition part 40 of the data acquisition unit 10. In step S1, the moving image data of the two-dimensional light image is acquired (moving-image acquisition step). The two-dimensional light image is an image including light from the sample S including the myocardial cell held inside the well 21 of the micro plate 20 by using the data acquisition unit 10. The moving image data refers to a group of two-dimensional image data obtained by temporally arranging the two-dimensional image data detected at predetermined time intervals. The moving image data enables the extraction of a temporal change in the luminance value of each pixel configuring the two-dimensional image.

First, a two-dimensional image of the micro plate 20 in which the sample S including the myocardial cell is held inside the well 21 is detected by the image pickup device 45 of the moving-image acquisition part 40 so as to acquire the moving image data. The moving image data is acquired only during a previously set time. A timing at which the acquisition of the moving image data is begun may be before applying a stimulation by the drug administration to the sample S in the well 21. The timing may be after applying a stimulation to the sample S in the well 21. The stimulation may be applied by the drug administration during the acquisition of the moving image data. The acquired moving image data is input to the data analysis device 50 from the data acquisition unit 10.

Step S11 is executed by the data analysis device 50. In step S11, the analysis processing is performed on the moving image data acquired in step S10 by the data acquisition unit 10 (analysis processing step). Step S11 includes a step of specifying a target pixel to be analyzed (region specifying step) and a step of implementing analysis processing on the target pixel (data processing step).

Step S20 is executed by the region specifying part 52 of the data analysis device 50. In step S20, on the basis of the luminance value data in the pixel of the moving image data acquired in step S10, the target pixel to be analyzed is specified. Step S20 includes a luminance-value-data acquisition step S21, a luminance-value extraction step S22 and a pixel specifying step S23. In the luminance-value-data acquisition step S21, luminance value data for each pixel is acquired. In the luminance-value extraction step S22, the peak value and the bottom value are acquired from the luminance value data of each pixel. In the pixel specifying step S23, on the basis of the peak value and the bottom value, the target pixel is specified.

Figure 6:
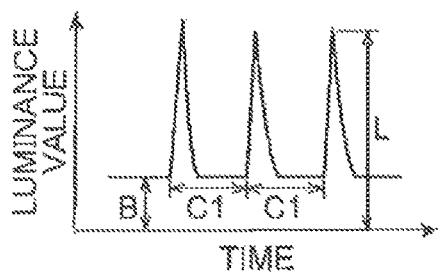
FIG. 6 is a diagram for describing an example of luminance value data.
Figure 6:
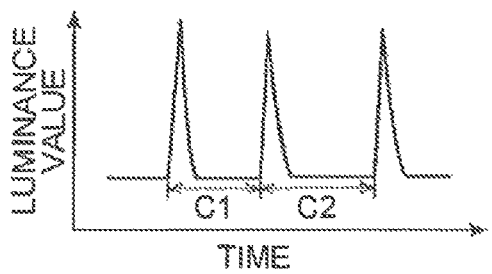
Figure 6:
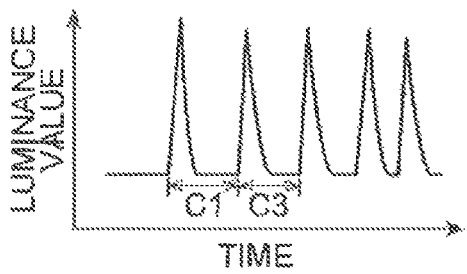
Figure 6:
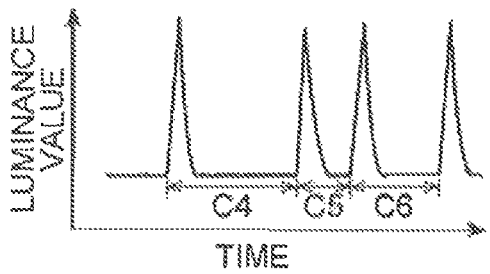
Figure 6:
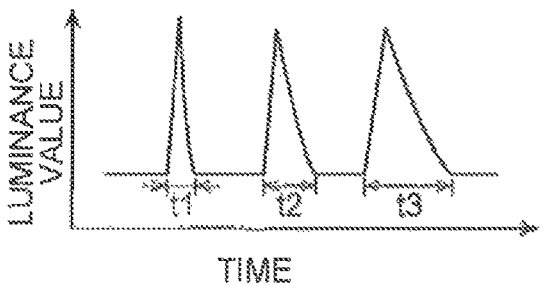

Step S21 is executed by the luminance-value-data acquisition part 52a. In step S21, the luminance value data for each pixel is acquired. A specific example of a repeatedly appearing temporal alteration in the luminance value will be described. A specific example of the repeatedly appearing temporal alteration in the luminance value is shown in a temporal alteration in the luminance value of five graphs shown in FIG. 6. With reference to FIG. 6(a), in the luminance value data, the luminance value may change in a fixed cycle. At this time, a cycle C1 is about one second. On the other hand, in the luminance value data, a cycle in which a peak of the luminance value appears may change with a lapse of time. FIG. 6(b) shows a case where a cycle in which the peak of the luminance value appears is longer with a lapse of time, and a cycle C2 is longer than the cycle C1. FIG. 6(c) shows a case where a cycle in which the peak of the luminance value appears is shorter with a lapse of time, and a cycle C3 is shorter than the cycle C1. FIG. 6(d) shows a case where a cycle in which the peak of the luminance value appears changes irregularly. With reference to FIG. 6(e), a case is shown where times t1, t2 and t3, i.e., a time while the luminance value changes from the bottom value to the peak value, then returns to the bottom value, are longer with a lapse of time. Examples of the repeatedly appearing temporal alteration in the luminance value are not limited to those shown in FIG. 6.

With reference to FIG. 5, step S22 is executed by the luminance-value extraction part 52b. In step S22, the peak value and the bottom value are extracted from the luminance value data acquired in step S21. A plurality of peak values are extracted as a result of a temporal alteration in the luminance value data in one pixel. A plurality of bottom values are extracted as a result of a temporal alteration in the luminance value data in one pixel.

Step S23 is executed by the pixel specifying part 52c. In step S23, on the basis of the peak value and the bottom value acquired in step S22, the target pixel configuring an image of a myocardial cell is specified. An evaluation value evaluating a state of the temporal alteration, of the luminance value, that repeatedly appears is calculated. The evaluation value includes a peak value, an amplitude of the luminance value and a change ratio (ratio value) of the luminance value, for example. With reference to FIG. 6(a), the peak value refers to an absolute value L of a peak appearing in the luminance value data. The bottom value is an absolute value B of a bottom appearing in the luminance value data. For the bottom value, luminance value data of a background acquired in advance may be used as the bottom value. The amplitude of the luminance value is a difference (L-B) between the peak value and the bottom value. The change ratio of the luminance value is a ratio (L/B) of the peak value relative to the bottom value.

To specify the target pixel, at least one of the evaluation values is used from among the above-described evaluation values. For example, as the evaluation value used for specifying the target pixel, the following combinations of (i) to (vi) are given:

(i) only the amplitude of the luminance value is used as the evaluation value;

(ii) only the change ratio of the luminance value is used as the evaluation value;

(iii) the peak value and the amplitude of the luminance value are used as the evaluation value;

(iv) the peak value and the change ratio of the luminance value are used as the evaluation value;

(v) the amplitude of the luminance value and the change ratio of the luminance value are used as the evaluation value; and (vi) the peak value, the amplitude of the luminance value and the change ratio of the luminance value are used as the evaluation value.

In comparison between the evaluation value and the threshold value, on the basis of the number of times that the evaluation value exceeds a threshold value set in advance, the target pixel is specified. For example, when a plurality of evaluation values provided in one pixel exceeds the threshold value n times (n is an integer of 1 or more), the one pixel is specified as the target pixel. It may be possible to specify the target pixel by comparing an average value of the evaluation values and the threshold value set in advance. For example, an average value of a plurality of evaluation values provided in one pixel is calculated. When the average value exceeds the threshold value, the one pixel is specified as the target pixel. Thus, the repeatedly appearing temporal alteration in the luminance value is evaluated on the basis of the evaluation value.

When a plurality of evaluation values are used to specify the target pixel as in the above-described (iii) to (vi), if all the evaluation values used for specifying the target pixel satisfy the condition defined by the threshold value, the pixel is specified as the target pixel.

Step S30 is executed by the data processing part 53. In step S30, the analysis processing is implemented on the target pixel configuring the image of the myocardial cell specified in step S20. Step S30 includes a correction step S31 and a luminance value data processing step S32. In the correction step S31, the luminance value data of the target pixel is corrected. In the luminance value data processing step S32, the data processing is performed on the basis of the corrected luminance value data.

Step S31 is executed by the phase correction part 53a. In step S31, a timing at which the luminance value changes from the bottom value to the peak value is corrected so as to calculate the corrected luminance value data. Depending on a location of the myocardial cell or a drug administration, in the temporal alteration in the luminance value radiated from the myocardial cell, there is a case where a timing at which the reaction appears lags depending on how the stimulation is transmitted. For example, a timing at which the reaction appears in a pixel configuring an image of a myocardial cell located away from the center of a stimulation lags behind a timing at which the reaction appears in a pixel located closer to the center of the stimulation. Therefore, the phase correction part 53a corrects to match a timing at which the luminance value changes from the bottom value to the peak value among a plurality of pixels. This enables an improvement in the measurement sensitivity. If the timing lag is within a time range set in advance, step S31 may be omitted.

Step S32 is executed by the luminance-value-data processing part 53b. In step S32, on the basis of the corrected luminance value data, processing of the luminance value data is performed. In the processing, for example, processing of calculating, in each time, the averaged luminance value data obtained by averaging the luminance value data of the target pixel in the well 21 for each two-dimensional image data is performed. This enables calculation of an average luminance of the light emitted from the cell in a certain time. The averaged luminance value data in each time is calculated by using the corrected luminance value data corrected in phase in step S31, and, it is thus possible to improve the measurement sensitivity. When there are a plurality of myocardial cells in the well 21, it may be possible to calculate the averaged luminance data obtained by averaging the luminance value data of the target pixel for each region of the myocardial cell configured by the target pixel.

Figure 7:
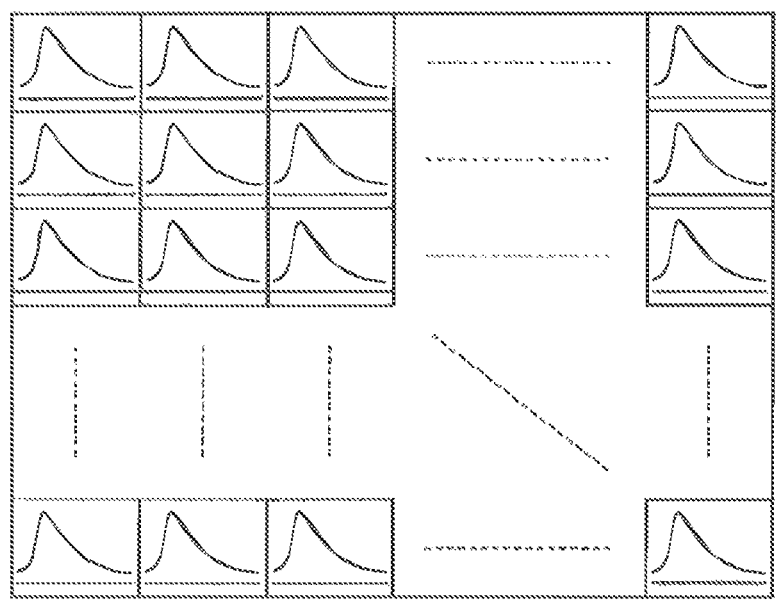
FIG. 7 is a diagram showing one example of a display of analysis results.

As a result of each of the above-described steps being implemented, the averaged luminance value data for each well 21 or each myocardial cell region is acquired. When analysis results for each well are is displayed on the display device 61, a screen shown in FIG. 7 is divided into a plurality of two-dimensionally arrayed display regions (in FIG. 7, 8×12=96 display regions), and a temporal change in the averaged luminance value data in the wells 21 corresponding to the respective display regions may be displayed.

In step S32, it may calculate the change ratio of the luminance value for each well 21. When the change ratio of the luminance value for each well 21 is calculated, the luminance value data of the target pixel in the well 21 are averaged. Next, the peak value and the bottom value are extracted from the averaged luminance value data, and the change ratio of the luminance value may be calculated. The peak value and the bottom value for each pixel are extracted from the luminance value data for each pixel and the change ratio of the luminance value for each pixel is calculated after which the change ratio of the luminance value for each pixel may be averaged.

The above-described light measurement method can be used for measuring a heart-beat cycle of the myocardial cell in the evaluation of the myocardial cell, for example.

A light measurement program for causing a computer to operate as the light measurement device 1 will be described below.

A light measurement program according to one embodiment is provided by being stored in a recording medium. Examples of the recording medium include a recording medium such as a floppy (registered trademark) disk, a CD-ROM, a DVD or a ROM, or a semiconductor memory.

Figure 8:
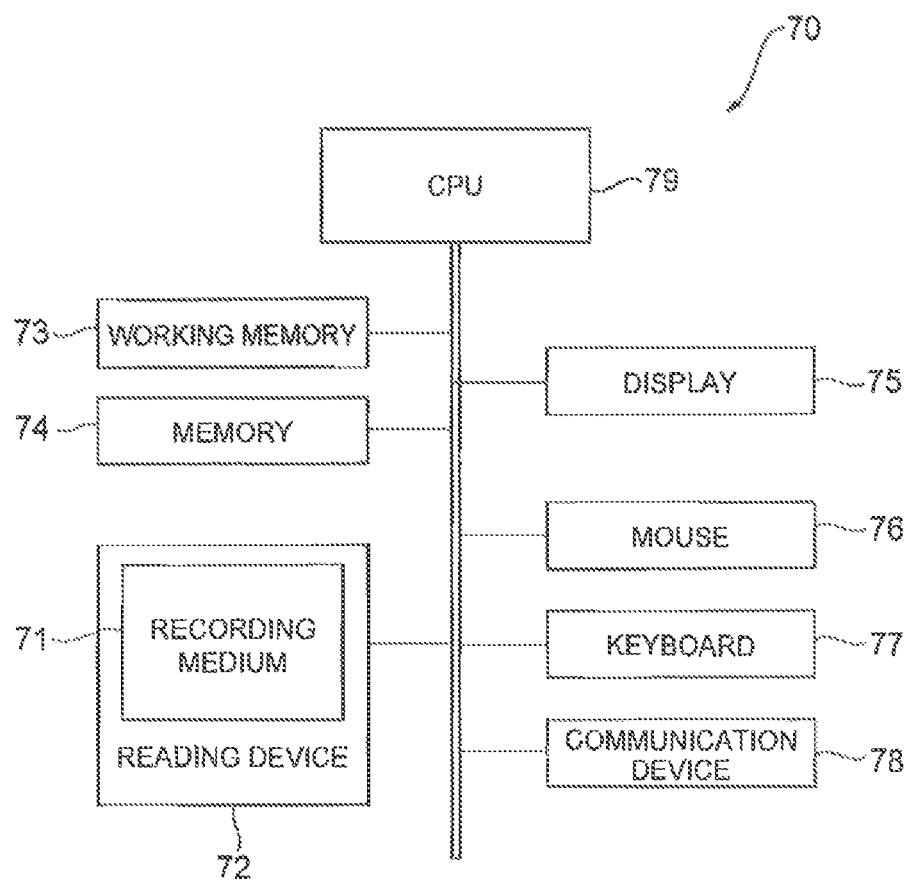
FIG. 8 is a diagram showing a hardware configuration of a computer for executing a program recorded on a recording medium.
Figure 9:
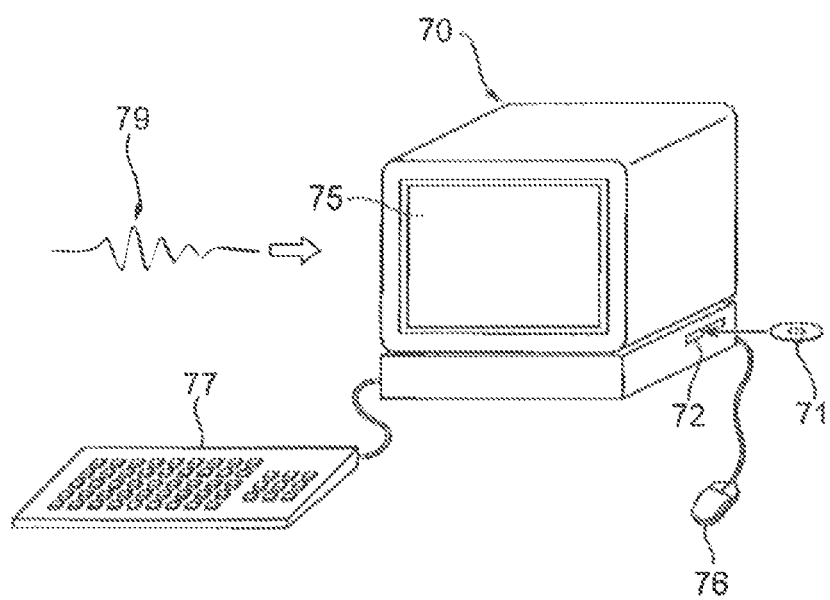
FIG. 9 is a diagram showing a computer for executing a program recorded on a recording medium.

FIG. 8 is a diagram showing a hardware configuration of a computer for executing a program recorded on a recording medium. FIG. 9 is a diagram of a computer for executing a program recorded on a recording medium. As the computer, various types of data processing devices that are provided with a CPU and that are for performing processing or control by software, such as a server device and a personal computer, are included.

As shown in FIG. 8, a computer 70 is provided with a reading device 72 such as a floppy (registered trademark) disk drive device, a CD-ROM drive device and a DVD drive device, a working memory (RAM) 73 in which an operating system permanently resides, a memory 74 for storing a program stored on a recording medium 71, a display device 75 such as a display, a mouse 76 and a keyboard 77 that are input devices, a communication device 78 for transmitting and receiving data, etc., and a CPU 79 for controlling the execution of a program. The computer 70 allows access from the reading device 72 to the light measurement program which is stored in the recording medium 71 upon insertion of the reading medium 71 into the reading device 72, and becomes operable by the light measurement program as the light measurement device 1 according to the present embodiment.

As shown in FIG. 9, the light measurement program may be provided as a computer data signal 79 superimposed on a carrier wave via a network. In this case, the computer 70 stores the light measurement program received by the communication device 78 into the memory 74, and can execute the light measurement program.

In the light measurement device 1 and the light measurement method according to one embodiment, the moving image data of the two-dimensional light image for each region corresponding to a plurality of wells 21 is acquired (S10), a luminance value data indicating a temporal alteration in the luminance value in each of a plurality of pixels configuring the moving image data is acquired (S21), and the peak value and the bottom value of the luminance value are extracted from the luminance value data (S22). Then, in the light measurement device 1 and the light measurement method, the evaluation value evaluating a state of a change in the luminance value on the basis of the peak value and the bottom value is calculated, and on the basis of a repeat state of the evaluation value, the target pixel configuring the image of a myocardial cell to be analyzed is specified from a plurality of pixels (S23). Thus, in the light measurement device 1 and the light measurement method, the target region is specified on the basis of the temporal alteration in the luminance value provided in the pixel. Therefore, in the light measurement device 1 and the light measurement method, it is possible to specify the pixel configuring the image of the myocardial cell from which light having a temporally altering luminance value is repeatedly emitted. Further, in the light measurement device 1 and the light measurement method, the target pixel is specified on the basis of the luminance value data indicating a temporal alteration in the luminance value, and, it is therefore possible to easily specify a boundary of the myocardial cell even when a region of a cell changes due to a beat as in a myocardial cell.

In the light measurement device 1, the evaluation value may be an amplitude of the luminance value obtained from a difference between the peak value and the bottom value. According to the evaluation value, the amplitude of the luminance value is zero in a pixel in a region having a fixed luminance value, and, when a threshold value of the amplitude is set, it thus becomes possible to specify only a pixel having an amplitude of the luminance value equal to or more than the threshold value. Therefore, it is possible to preferably specify the pixel configuring the image of the myocardial cell from which light having a temporally altering luminance value is repeatedly emitted.

In the light measurement device 1, the evaluation value may be a change ratio of the luminance value obtained from a ratio of a peak value relative to a bottom value. According to the evaluation value, the change ratio of the luminance value in the pixel in a region having a fixed luminance value is 1, and, when a threshold value of the change ratio is set, it thus becomes possible to specify only a pixel having a change ratio of the luminance value equal to or more than a threshold value. Therefore, it is possible to preferably specify the pixel configuring the image of the myocardial cell from which light having a temporally altering luminance value is repeatedly emitted.

In the light measurement device 1, the pixel specifying part 52c may specify the target pixel on the basis of the number of times that the evaluation value exceeds a threshold value acquired in advance. According to the method, it is possible to more preferably specify a pixel configuring an image of a myocardial cell from which light having a temporally altering luminance value is repeatedly emitted.

In the light measurement device 1, the pixel specifying part 52c may specify the target pixel by comparing the average value of the evaluation value and the threshold value acquired in advance. It is possible to more preferably specify a pixel configuring an image of a myocardial cell from which light having a temporally altering luminance value is repeatedly emitted.

In the light measurement device 1, the analysis processing part 51 may further include a data processing part 53 for using, as the analysis data, the luminance value data of a target pixel and performing analysis processing on luminance value data. According to the configuration, it is possible to evaluate the sample S by using the luminance value data of the pixel selected by the pixel specifying part 52c. Therefore, it is possible to perform analysis processing in which the sensitivity to the light from the sample S is improved. That is, the pixel having the luminance value data that temporally alters in a similar manner is specified on the basis of the luminance value data for each pixel so as to calculate an average, therefore, as compared to a case where a region occupied by one well 21 is regarded as one analysis region, it is possible to perform analysis processing in which the sensitivity to the light from the pixel configuring the image of the myocardial cell is improved.

Next, an example where the light measurement device 1 is used for evaluating a cell will be described.

In one embodiment, for the evaluation value, the peak value, the amplitude of the luminance value, and the change ratio of the luminance value are used. For the evaluation value, the cycle of the luminance value may be used. For the evaluation value, a temporal alteration in an area provided in the region configured by a plurality of target pixels may be used. Further, in one embodiment, analysis processing may be performed by combining a plurality of evaluation values from among the peak value, the amplitude of the luminance value, the change ratio of the luminance value, the cycle of the luminance value and the temporal alteration in the area. Further, the presence or absence of Fluorescence Resonance Energy Transfer (FRET) reaction, obtained on the basis of the image in which two luminance value data are displayed may be used for specifying the target pixel.

Figure 10:
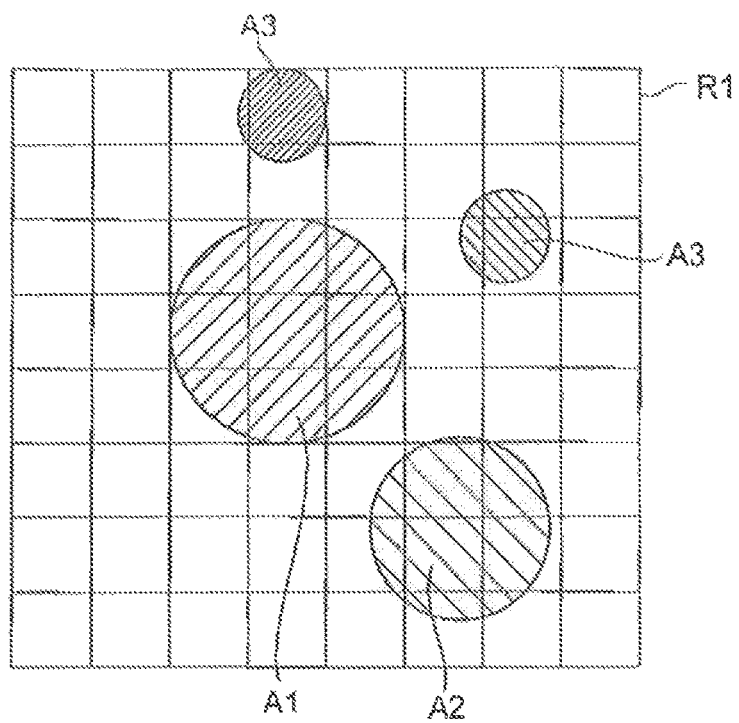
FIG. 10 is a diagram for describing one application example of a light measurement method.
Figure 10:
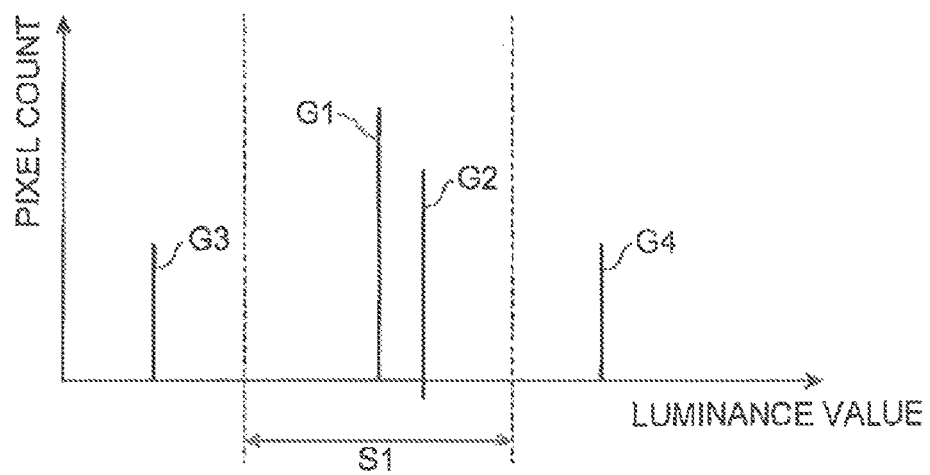

As shown in FIG. 10(a), when the presence or absence of the cell in a measurement region R1 is determined, for example, the peak value may be used as the evaluation value. In the measurement region R1, there is a region A1 of a myocardial cell, a region A2 of a cell other than a myocardial cell and a region A3 of a plurality of dust. One region of a plurality of squares included in the measurement region R1 corresponds to one pixel. At this time, when the number of pixels including respective elements is plotted against the luminance values of the pixels including the respective elements, the results are obtained as shown in FIG. 10(b). A graph G1 shows the frequency of luminance values in the region A1 of a myocardial cell. A graph G2 shows the frequency of luminance values in the region A2 of a cell other than a myocardial cell. When a range S1 of a predetermined luminance value is set, it becomes possible to specify the pixel included in the images in the region A1 of a myocardial cell and the region A2 of a cell other than a myocardial cell from the measurement region R1.

Figure 11:
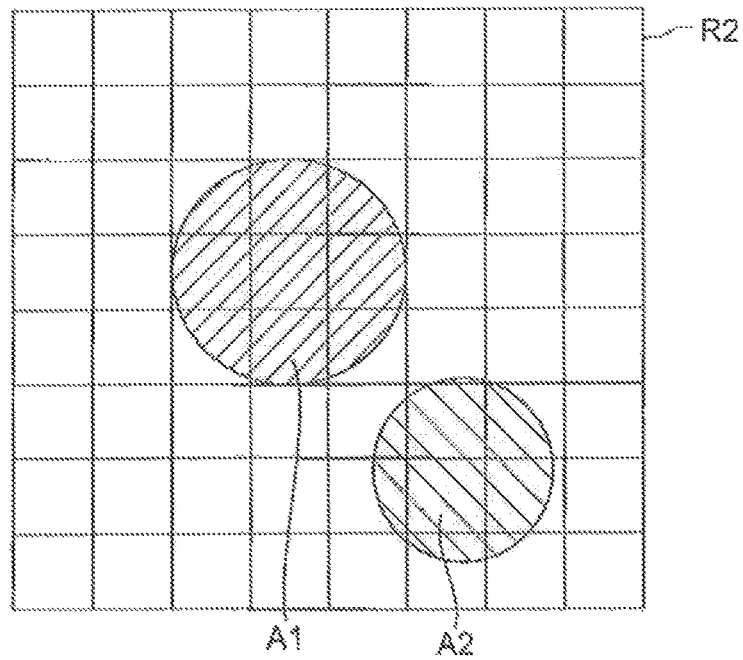
FIG. 11 is a diagram for describing another application example of a light measurement method.
Figure 11:
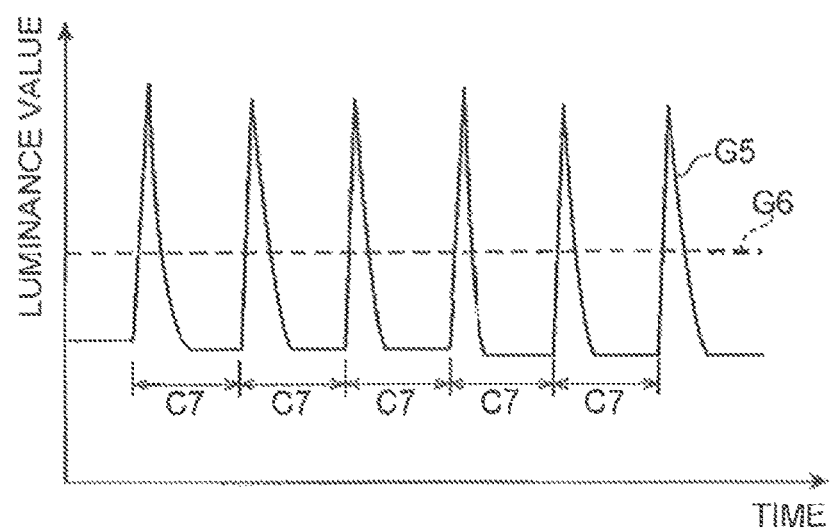

As shown in FIG. 11(a), in a region including different types of cells, for example, when the myocardial cell is specified, it is possible to use the amplitude of the luminance value or the change ratio of the luminance value, as the evaluation value. In the measurement region R2, there is a region A1 of a myocardial cell and a region A2 of a cell other than a myocardial cell. The myocardial cell beats. In response to the beat, as shown in a graph G5 in FIG. 11(b), the luminance value of the pixel included in the region A1 changes in terms of time. On the other hand, the cell other than the myocardial cell does not beat, therefore, as shown in a graph G6, the luminance value is constant. Therefore, when the amplitude of the luminance value or the change ratio of the luminance value is used, it is possible to specify from the measurement region R2 the pixel included in the image of the region A1 of a myocardial cell. The myocardial cell beats in a fixed cycle C1, and, when the cycle of the luminance value is used, it is therefore possible to specify more reliably the pixel included in the image in the region A1 of the myocardial cell.

Figure 12:
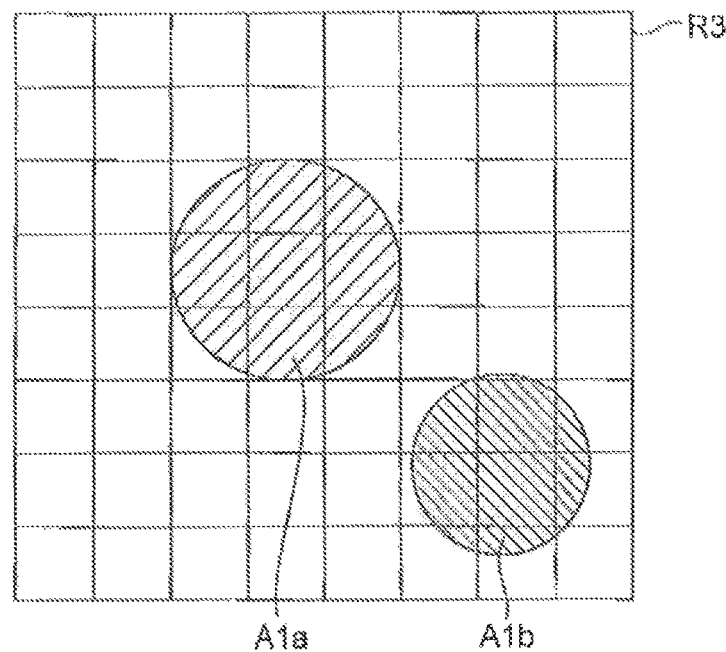
FIG. 12 is a diagram for describing still another application example of a light measurement method.
Figure 12:
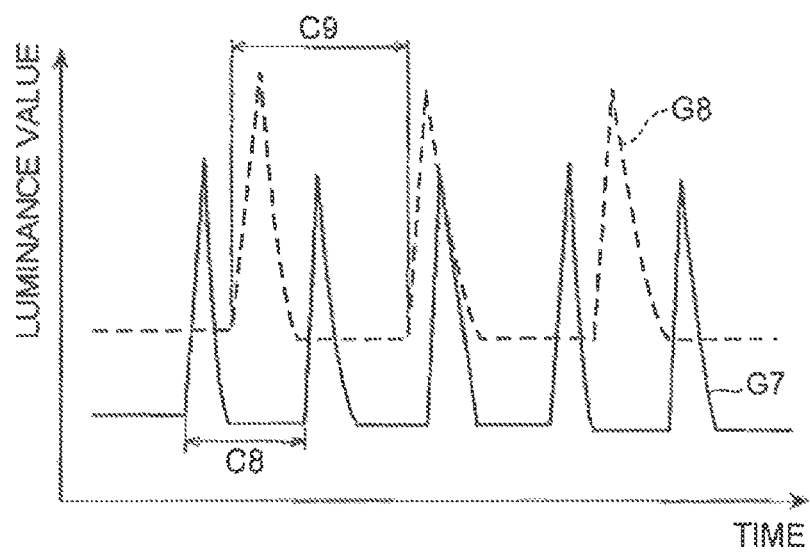

As shown in FIG. 12(a), when a region A1a of a desired myocardial cell is specified in the region R3 including a plurality of myocardial cells, the cycle of the luminance value may be used as the evaluation value. A graph G7 in FIG. 12(b) shows a temporal alteration in the luminance value of the pixel included in the region A1a of the myocardial cell, and a graph G8 shows a temporal alteration in the luminance value of the pixel included in a region A1b of the myocardial cell. For example, a cycle C8 of the luminance value in the region A1a of the myocardial cell is different from a cycle C9 of the luminance value in the region A1b of the myocardial cell. Therefore, by comparing the cycle C8 and the cycle C9, it is possible to specify the desired myocardial cell. According to the method, it is possible to exclude a myocardial cell not appropriate to the analysis from among the myocardial cells. The method can be used for implementing a screening in which a more preferable analysis target is specified.

When a cell is distinguished in a region including a plurality of respectively different myocardial cells and a cell other than a myocardial cell, the peak value, either one of the amplitude of the luminance value or the change ratio of the luminance value and the cycle of the luminance value can be used in combination as the evaluation value. When the peak value is used, it becomes possible to specify a cell exceeding a predetermined peak-value threshold value. That is, it is possible to specify a cell with a good stained condition. When either one of the amplitude of the luminance value or the change ratio of the luminance value is used, it becomes possible to distinguish the myocardial cell from a cell other than a myocardial cell. Then, when the cycle of the luminance value is used, it becomes possible to distinguish one myocardial cell from another myocardial cell.

Figure 13:
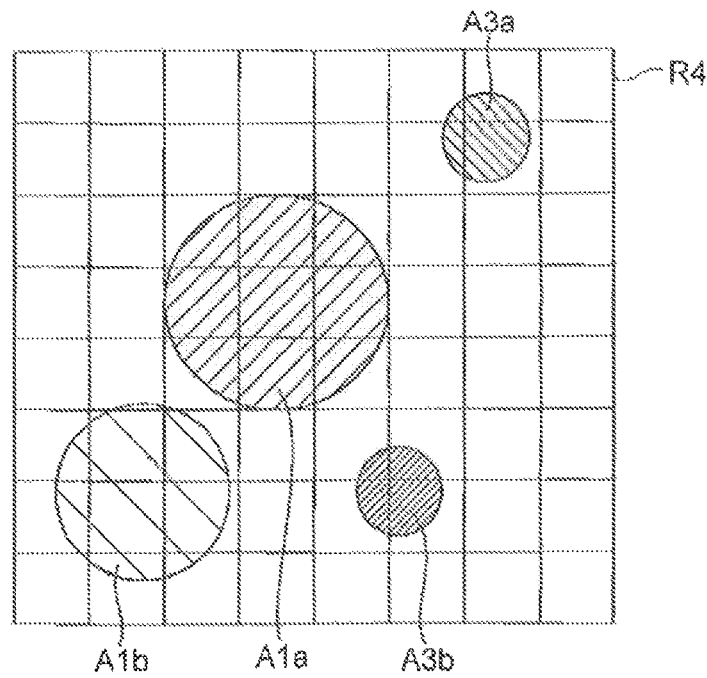
FIG. 13 is a diagram for describing still another application example of a light measurement method.
Figure 13:
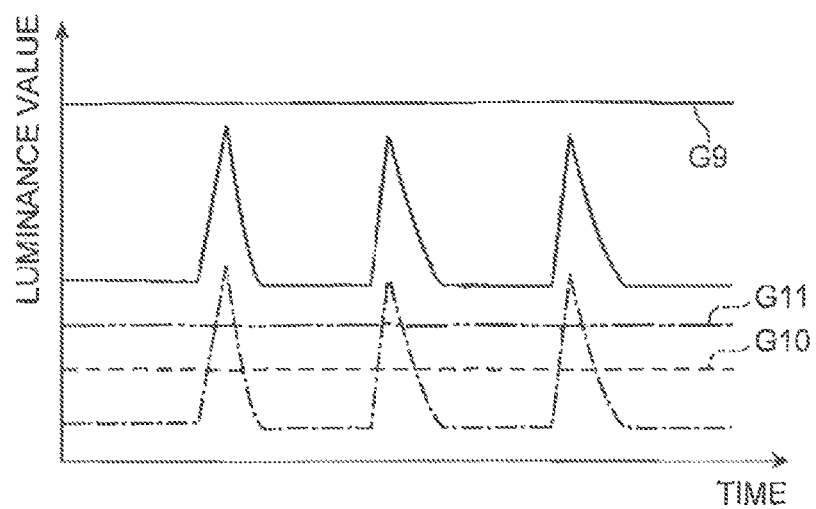

As shown in FIG. 13(a), when regions A3a and A3b of a dust and a background that cannot be the target of analysis are specified from a measurement region R4, it is possible to use the peak value, the amplitude of the luminance value, the change ratio of the luminance value, and the cycle of the luminance value, as the evaluation value. For example, with reference to FIG. 13(b), a graph G9 indicating the luminance value data of the region A3a is saturated, thus, the data cannot be the target of analysis. Therefore, the region A3a is excluded as a dust or a background. A graph G10 indicating the luminance value data of the region A3b has a value falling below a peak-value threshold value G11, thus, the data cannot be the target of analysis. Therefore, the region A3b is excluded as a dust or a background.

Figure 14:
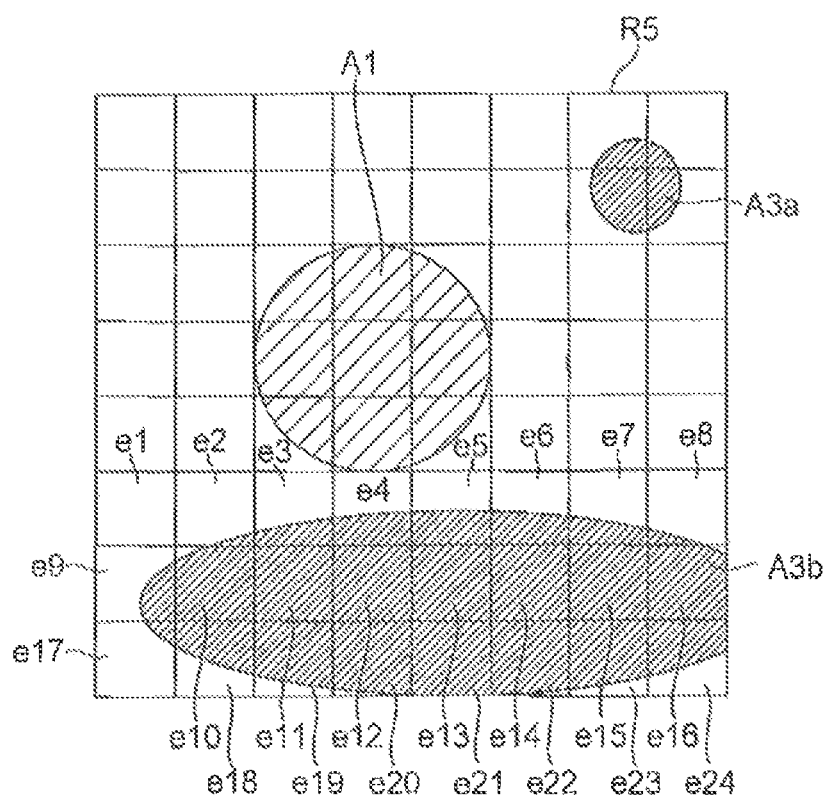
FIG. 14 is a diagram for describing still another application example of a light measurement method.

As shown in FIG. 14, when the regions A3a and A3b of a dust that cannot be the target of analysis are specified from a measurement region R5, the area of the region configured by the target pixel can be used as the evaluation value. For example, the region A3b comprising a plurality of pixels e1 to e24 specified as the target pixel has a very large area relative to the region A1 of the myocardial cell. It is unlikely that the region A3b having such a very large area is a myocardial cell, etc. Therefore, it is possible to specify the region A3b of a dust that cannot be the target of analysis.

When the evaluation is performed on the basis of the luminance value data of the target pixel configuring an image of a myocardial cell, the light measurement device 1 may detect the number of beats of the myocardial cell on the basis of the cycle of the luminance value. The light measurement device 1 may also determine a state of an irregular pulse on the basis of the change ratio and the cycle of the luminance value. The light measurement device 1 may determine an effect of a medicament administered to a cell on the basis of the change ratio and the cycle of the luminance value.

REFERENCE SIGNS LIST

1 . . . light measurement device, 20 . . . micro plate, 21 . . . well, 40 . . . moving-image acquisition part, 50 . . . data processing device, 51 . . . analysis processing part, 52a . . . luminance-value-data acquisition part, 52b . . . luminance-value extraction part, 52c . . . pixel specifying part, S . . . sample.

The invention claimed is:

1. A light measurement apparatus for measuring light from a sample including a myocardial cell, comprising:
at least one non-transitory memory storing instructions; and
one or more hardware processors that are coupled to the at least one non-transitory memory and that are configured to execute the instructions to cause the system to perform operations comprising:
acquiring luminance-value data from a pixel of an image of the sample over time, wherein the image of the sample comprises an image of the myocardial cell, the pixel is associated with a location within the sample, and the acquired luminance-value data indicates a cyclical temporal alteration in light detected at the location of the sample, evaluate the cyclical temporal alteration being detected by detecting cycles of the luminance-value data with at least one threshold associated with the pulsing of the myocardial cell;
determining the cyclical temporal alteration by extracting a plurality of peak values of the luminance value from the luminance-value data;
calculating at least one evaluation value for each of the cycles of the luminance-value data;
calculating the number of times the peak value exceeds the threshold by comparing the peak value with the threshold value;
determining an average value from the at least one evaluation value calculated for each of the cycles of the luminance-value data;
determining the presence of the myocardial cell at the location of the sample by comparing the average value with the at least one threshold; and
identifying a target pixel based on the number of times the peak value exceeds the threshold value, the target pixel forming at least a part of the image of the myocardial cell.

2. The light measurement apparatus according to claim 1, wherein the operations further comprise:
determining a reaction of the myocardial cell to a medicament administered to the myocardial cell.

3. A light measurement method for measuring light from a sample including a myocardial cell, comprising:

acquiring luminance-value data from a pixel of an image of the sample over time, wherein the image of the sample comprises an image of the myocardial cell, the pixel is associated with a location within the sample, and the acquired luminance-value data indicates a cyclical temporal alteration in light detected at the location of the sample, determining a presence of the myocardial cell at the location of the sample by detecting cycles of the luminance-value data corresponding to a pulsing of the myocardial cell, based on a comparison of the luminance-value data with at least one threshold associated with the pulsing of the myocardial cell to obtain the cyclical temporal alteration, determining the cyclical temporal alteration by extracting a plurality of peak values of the luminance value from the luminance-value data, calculating at least one evaluation value for each of the cycles of the luminance-value data, calculating the number of times the peak value exceeds the threshold by comparing the peak value with the threshold value, determining an average value from the at least one evaluation value calculated for each of the cycles of the luminance-value data, determining the presence of the myocardial cell at the location of the sample by comparing the average value with the at least one threshold, and identifying a target pixel based on the number of times the peak value exceeds the threshold value, the target pixel forming at least a part of the image of the myocardial cell.

4. A non-transitory computer readable medium having stored thereon one or more sequences of instructions for causing one or more processors to perform the steps for measuring light from a sample including a myocardial cell, the steps comprising:

acquiring luminance-value data from a pixel of an image of the sample over time, wherein the image of the sample comprises an image of the myocardial cell, the pixel is associated with a location within the sample, and the acquired luminance-value data indicates a cyclical temporal alteration in light detected on the location of the sample, evaluating the determining a presence of the myocardial cell at the location of the sample by detecting cycles of the luminance-value data corresponding to a pulsing of the myocardial cell, based on a comparison of the luminance-value data with at least one threshold associated with the pulsing of the myocardial cell to obtain the cyclical temporal alteration, identifying the pixel associated with the luminance-value data as a target pixel that forms at least part of the image of the myocardial cell, determining the cyclical temporal alteration by extracting a plurality of peak values of the luminance value from the luminance-value data, calculating at least one evaluation value for each of the cycles of the luminance-value data, calculating the number of times the peak value exceeds the threshold by comparing the peak value with the threshold value, and determining an average value from the at least one evaluation value calculated for each of the cycles of the luminance-value data, determining the presence of the myocardial cell at the location of the sample by comparing the average value with the at least one threshold, and identifying the target pixel based on the number of times the peak value exceeds the threshold value.

* * * * *